(12) United States Patent
Hunt et al.

(10) Patent No.: US 11,022,975 B2
(45) Date of Patent: Jun. 1, 2021

(54) SYSTEMS AND METHODS FOR OPERATING AN AUTONOMOUS VEHICLE IN A PRESENCE OF HAZARDOUS MATERIALS

(71) Applicant: Rivian IP Holdings, LLC, Plymouth, MI (US)

(72) Inventors: Patrick Hunt, Evanston, IL (US); Justin Wade, San Jose, CA (US); Lacey Trelfa, Ypsilanti, MI (US)

(73) Assignee: Rivian IP Holdings, LLC, Plymouth, MI (US)

( * ) Notice: Subject to any disclaimer, the term of this patent is extended or adjusted under 35 U.S.C. 154(b) by 137 days.

(21) Appl. No.: 16/006,544

(22) Filed: Jun. 12, 2018

(65) Prior Publication Data

US 2019/0377350 A1    Dec. 12, 2019

(51) Int. Cl.
*G05D 1/00* (2006.01)
*G05D 1/02* (2020.01)
*G01N 33/497* (2006.01)

(52) U.S. Cl.
CPC ......... *G05D 1/0214* (2013.01); *G01N 33/497* (2013.01); *G05D 1/0088* (2013.01); *G05D 2201/0212* (2013.01)

(58) Field of Classification Search
CPC ............. G05D 1/0214; G05D 1/0088; G05D 2201/0212; G01C 21/3415; G01N 33/497
See application file for complete search history.

(56) References Cited

U.S. PATENT DOCUMENTS

| 2005/0253699 A1* | 11/2005 | Madonia ............... B60K 35/00 340/463 |
| 2013/0070043 A1* | 3/2013 | Geva ................... B60K 28/066 348/14.02 |
| 2013/0185866 A1* | 7/2013 | Cheung ................ E04H 1/1216 4/662 |

(Continued)

FOREIGN PATENT DOCUMENTS

| EP | 3 330 827 | 6/2018 |
| JP | 2018032436 | 3/2018 |
| WO | WO 2016064581 | 4/2016 |

OTHER PUBLICATIONS

Sasidharan Shyma et al., Vehicle cabin safety alert system, 2015 International Conference on Computer Communication and Informatics (ICCCI), IEEE Jan. 8, 2016 pp. 1-4.

(Continued)

*Primary Examiner* — Anshul Sood
(74) *Attorney, Agent, or Firm* — Haley Guiliano LLP

(57) ABSTRACT

Systems and methods are provided herein for operating an autonomous vehicle in the presence of hazardous materials. The autonomous vehicle is operated in travel along a selected route. A determination is made, using a sensor, that a hazardous material is present inside the autonomous vehicle during the operation of the autonomous vehicle. In response, a setting of the autonomous vehicle is changed to counteract the presence of the hazardous material inside the autonomous vehicle. Additionally, also in response, a modified route is calculated, the modified route addressing the presence of the hazardous material inside the autonomous vehicle. Then, the autonomous vehicle is operated to travel along the modified route.

18 Claims, 7 Drawing Sheets

(56) References Cited

U.S. PATENT DOCUMENTS

| | | | |
|---|---|---|---|
| 2013/0325323 A1 | 12/2013 | Breed | |
| 2016/0303969 A1* | 10/2016 | Akula | A61B 5/6893 |
| 2018/0075565 A1* | 3/2018 | Myers | G06Q 30/02 |
| 2018/0116605 A1* | 5/2018 | Newberry | A61B 5/6893 |
| 2018/0136655 A1* | 5/2018 | Kim | B60R 25/23 |
| 2018/0266834 A1* | 9/2018 | Cronin | B60R 16/037 |
| 2019/0187704 A1* | 6/2019 | Gordon | G01C 21/3484 |
| 2019/0197325 A1* | 6/2019 | Reiley | G06Q 10/06 |
| 2019/0197868 A1* | 6/2019 | Guerin | G08B 21/14 |
| 2019/0378350 A1* | 12/2019 | DeRouen | G07C 5/0808 |

OTHER PUBLICATIONS

International Search Report and Written Opinion of PCT/US2019/036475 dated Oct. 18, 2019.

* cited by examiner

SYSTEMS AND METHODS FOR OPERATING AN AUTONOMOUS VEHICLE IN A PRESENCE OF HAZARDOUS MATERIALS

BACKGROUND

Current autonomous vehicle technology allows an autonomous vehicle to transport passengers between destinations without being directly controlled by a human driver. However, due to an absence of a driver, an autonomous vehicle may encounter unexpected or unusual circumstances that the autonomous vehicle may not be able to autonomously handle or mitigate. For example, the interior of the autonomous vehicle may become unpleasant or even unsafe due to presence of hazardous or biohazardous material. Current autonomous vehicles are unable to properly respond to such an occurrence, leading to an unpleasant or dangerous experience for an occupant.

SUMMARY

In accordance with the present disclosure, systems and methods are provided that improve the operation of an autonomous vehicle by providing techniques for autonomous handling of a situation where hazardous or biohazardous material is present inside of an autonomous vehicle. For example, when a hazardous material is detected inside of a vehicle, the autonomous vehicle may automatically take appropriate actions to mitigate the presence of a such a hazard. For example, the autonomous vehicle may increase the level of ventilation, open some or all of the windows, engage additional filters, or perform any combination of the above.

Some embodiments, described below, may be performed by a processing circuitry. The processing circuitry may be implemented as a part of an autonomous vehicle, a user device, a server, or as a part of a combination thereof. In some embodiments, the processing circuitry of the autonomous vehicle may operate the autonomous vehicle along a selected route. For example, the autonomous vehicle may be a taxi delivering a passenger to a requested destination.

In some embodiments, the processing circuitry may determine, using a sensor, a presence of hazardous material inside of the autonomous vehicle during the operation of the autonomous vehicle. For example, the processing circuitry may use a gas sensor to detected presence of urine or vomit.

In some embodiments, the processing circuitry may, in response to determining the presence of hazardous material, change a setting of the autonomous vehicle to counteract the presence of the hazardous material inside of the autonomous vehicle. For example, the processing circuitry may strategically open one or more windows, and/or increase air ventilation inside the car.

In some embodiments, the processing circuitry may, in response to determining the presence of hazardous material, calculate a modified route, wherein the modified route addresses the presence of the hazardous material inside the autonomous vehicle. For example, the processing circuitry may add an emergency stop to the current route or replace the current destination with an alternative stop. Alternatively, or additionally, the processing circuitry may modify the current destination to add a first-responder facility and/or a cleaning facility as a destination.

In some embodiments, the processing circuitry may then operate the autonomous vehicle to travel along the modified route. For example, the processing circuitry may pull the autonomous vehicle over to the shoulder to discharge the passenger and then proceed to a cleaning facility.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments. These drawings are provided to facilitate an understanding of the concepts disclosed herein and should not be considered limiting of the breadth, scope, or applicability of these concepts. It should be noted that for clarity and ease of illustration these drawings are not necessarily made to scale.

DETAILED DESCRIPTION

Figure 1A:
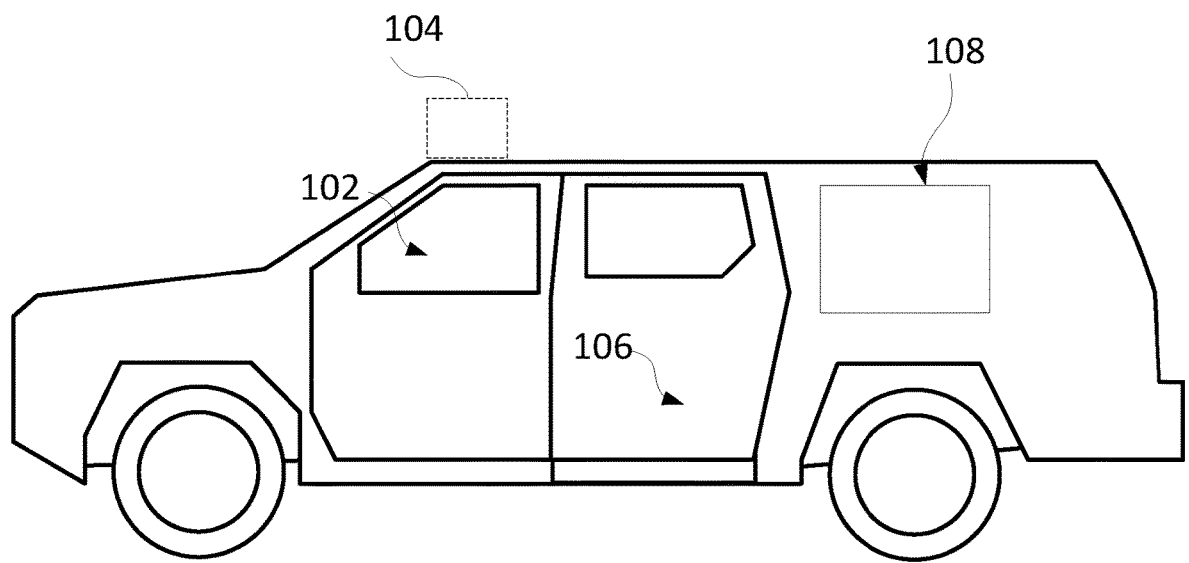
FIG. 1A shows a side view of an illustrative autonomous vehicle, in accordance with some embodiments of the present disclosure.

The present disclosure is directed to techniques for operating an autonomous vehicle in a hazard mode. In some embodiments, while an autonomous vehicle is operating along a selected route, a presence of a hazardous material may be detected. For example, the autonomous vehicle may use a gas sensor to detect a presence of a high concentration of a dangerous material. In this situation, the autonomous vehicle may begin operating to counteract the presence of the hazardous material. For example, the autonomous vehicle may increase air ventilation, engage additional filtering, open windows, provide breathing masks, take any other action to counteract the presence of the hazardous material, or perform any combination of the above. In addition, the autonomous vehicle may simultaneously modify the selected route to further address the presence of the hazardous material. For example, the autonomous vehicle may be re-routed to pull over, to discharge the passengers, and/or to proceed to a facility equipped to handle the hazardous material.

As referred to herein, the term "autonomous vehicle" refers to any kind of a transportation device (e.g., a car, a truck, a bus, an airplane, a boat, etc.) that may navigate, drive or move between geographical locations without direct control by a human operator or driver.

As referred to herein, the term "hazardous material" refers to any kind of a liquid, solid or gaseous material that presents any kind of hazard or discomfort to a human subject. For example, hazardous material may refer to gasses that create suffocation risks (e.g., CO or $CO_2$) gasses that create discomfort (e.g., hydrogen sulfide). Hazardous material may also refer to any kinds of liquids that are dangerous or unpleasant (e.g., highly acidic or basic liquids.) Hazardous material may also refer to solids that are dangerous or unpleasant (e.g., explosives, unstable compounds, etc.).

As referred to herein, the term "biohazardous material" refers to any kind of hazardous material that is biological in origin. Biohazardous material may refer to blood and blood products (both human and animal), animal and human waste, human bodily fluids, microbiological waste, and pathological waste.

As referred to herein, the term "human-generated biohazardous material" refers to any kind of biohazardous material that is human in origin. Human-generated biohazardous materials may include human blood, urine, vomit, stool, or any other hazardous or unpleasant gas, liquid or solid produced by a human body.

As referred to herein, the term "first-responder facility" refers to any kind of facility, building or site designed to provide at least one first-response service. For example, a first-responder facility may offer at least one of emergency room services, hospital services, police services, firefighting services, poison control service, hazmat disposal services, any other first-response service, or any combination of the above. In some embodiments, a first-responder facility may include a computer system for receiving and sending out information relating to the first-response services.

As referred to herein, the term "cleaning facility" refers to any kind of facility, building or site designed to provide at least one of cleaning of maintenance services to vehicles. For example, a cleaning facility may offer at least one of car wash services, interior cleaning services, mechanical services, hazmat disposal services, any other vehicle-related service, or any combination of the above. In some embodiments, a cleaning facility may include a computer system for receiving and sending out information relating to the cleaning services.

FIG. 1A shows a side view of an illustrative autonomous vehicle 100 in accordance with some embodiments of the present disclosure. In some embodiments, autonomous vehicle 100 may be a coupe, a sedan, a truck, a bus, or any other type vehicle. In some embodiments, autonomous vehicle 100 may have a capability of being operated without direct control by a human operator or driver.

In some embodiments, autonomous vehicle 100 may include a plurality of external sensors 104. For example, some of the external sensors 104 may be mounted on the roof of autonomous vehicle 100. In some embodiments, external sensors 104 may be attached to any other part of the autonomous vehicle 100. In some embodiments, external sensors 104 may include video sensors, audio sensors, gas sensors, pressure sensors, GPS sensors, LIDAR sensors, radar sensors, radio antennas, or any combination thereof.

In some embodiments, autonomous vehicle 100 may be capable of autonomous operation based on input received from external sensors 104. For example, autonomous vehicle 100 may use the GPS sensors to ascertain its geographical position, while the camera sensors, LIDAR sensors, and/or radar sensors may be used to detect the presence of other objects, enabling autonomous vehicle 100 to navigate to a destination while safely avoiding obstacles.

In some embodiments, autonomous vehicle 100 may include elements that may be directly controlled by autonomous vehicle 100 without human inputs. For example, autonomous vehicle 100 may include an engine, a transmission, wheel controls, turn signals, and other elements commonly found in vehicles. In some embodiments, autonomous vehicle 100 may directly control operation of such elements in order to autonomously operate (e.g., drive) autonomous vehicle 100 to a destination.

In some embodiments, autonomous vehicle 100 may include elements that are not directly used to drive autonomous vehicle 100. For example, autonomous vehicle 100 may include window 102 and door 106 (as well as other windows and doors). In some embodiments, autonomous vehicle 100 may have a capability to operate such elements. For example, autonomous vehicle 100 may have a capability to automatically open and close window 102 (as well other windows). In another example, autonomous vehicle 100 may have a capability to automatically open and close door 106 (as well other doors). In some embodiments, window 102 and door 106 (as well as other windows and doors) may have a capability to be operated by a human user. In some embodiments, autonomous vehicle 100 may have a capability to prevent the user from operating window 102 and door 106 (as well as other windows and doors) during certain periods of time (e.g., when it is unsafe to do so).

In some embodiments, autonomous vehicle 100 may include an external display 108. For example, display 108 may be a running-letter display, an LED display, or any other type of a display. In some embodiments, display 108 may be used to communicate messages or warnings. For example, display 108 may be used to indicate that autonomous vehicle 100 is operating in a hazard mode. For example, display 108 may display a message "WARNING! Hazard Inside." In some embodiments, display 108 may indicate the type and intensity of the present hazard.

Figure 1B:
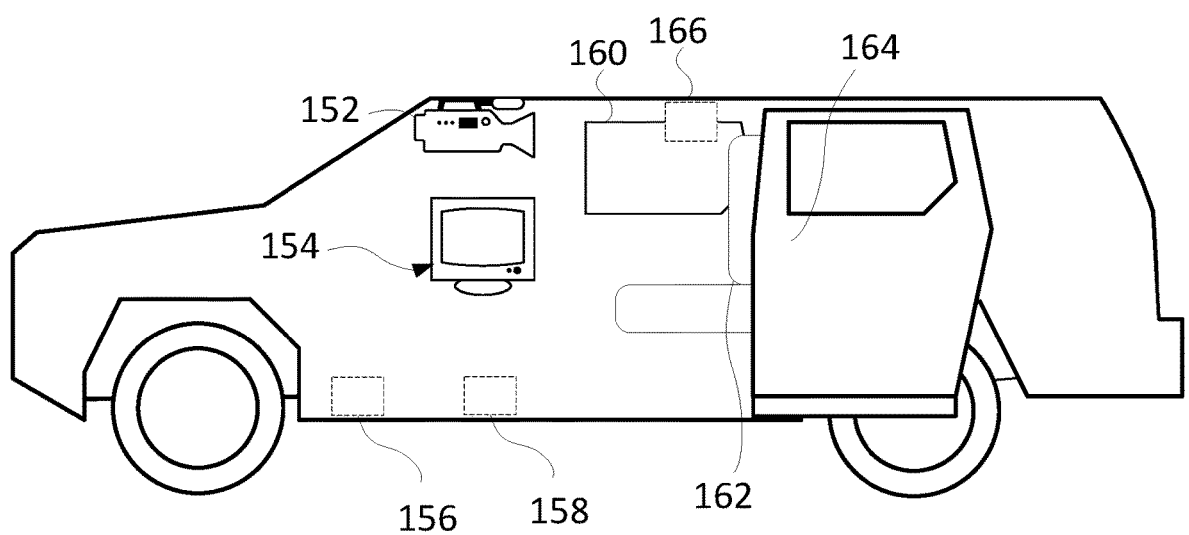
FIG. 1B shows another side view of an illustrative autonomous vehicle, in accordance with some embodiments of the present disclosure.

FIG. 1B shows another side view of illustrative autonomous vehicle 100 in accordance with some embodiments of the present disclosure. FIG. 1B, among other things, illustrates interior elements of exemplary autonomous vehicle 100.

In some embodiments, autonomous vehicle 100 may include a set of internal elements. In some embodiments, autonomous vehicle 100 may include circuitry 156 for controlling the operation of autonomous vehicle 100. For example, circuitry 156 may include a circuitry processor, a hardware processor, a software processor (e.g., a processor emulated using a virtual machine), or any combination thereof. In some embodiments, circuitry 156 may include non-transitory memory storing instructions, for operating autonomous vehicle 100. For example, the instructions when executed by the processor, may cause the processor to operate autonomous vehicle 100 in accordance with embodiments described above and below.

In some embodiments, circuitry 156 may be in communicative connection with some or all other elements of autonomous vehicle 100 shown in FIGS. 1A and 1B. For example, circuitry 156 may be connected to such elements via one or more wires, or by a wireless communication. In some embodiments, circuitry 156 may receive input from external sensors 104, process the input, and operate any one or all of: an engine, a transmission, wheel controls, turn signals, and other elements commonly found in vehicles in order to drive autonomous vehicle 100. In some embodiments, circuitry 156 may receive input from any other element of autonomous vehicle 100. In some embodiments, circuitry 156 may send commands to operate any other element of autonomous vehicle 100. In some embodiments, circuitry 156 may include communication elements (e.g., an antenna, a set of antennas, a set of transceivers) for communicating with other devices external to autonomous vehicle 100 (e.g., user devices, servers, third-party data providers, etc.)

In some embodiments, autonomous vehicle 100 may include an internal camera 152 (e.g., a video camera, an IR camera, any other camera, or any combination thereof). In some embodiments, camera 152 may be positioned to capture the current conditions of autonomous vehicle 100. In some embodiments, video camera 152 may provide a video feed to circuitry 156. In some embodiments, circuitry 156 may receive input from camera 152. In some embodiments, autonomous vehicle 100 may control camera 152. For example, autonomous vehicle 100 may control direction, focus, angle, any other feature of camera 152, or any combination thereof. In some embodiments, camera 152 may also include a microphone or another audio capture device. In some embodiments, autonomous vehicle 100 may separately include a microphone or another audio capture device.

In some embodiments, autonomous vehicle 100 may include a display 154. For example, display 154 may be an LCD display, an OLED display, an LED display, or any other type of display. In some embodiments, display 154 may be a touch screen display with input capabilities. In some embodiments, circuitry 156 may provide a picture output to display 154. In some embodiments, circuitry 156 may receive input from display 154 (e.g., user input received via a touch screen).

In some embodiments, display 154 may act as user interface for controlling autonomous vehicle 100. For example, display 154 may present an interface for the user to input a destination for autonomous vehicle 100. In some embodiments, display 154 may provide options to control other elements of autonomous vehicle 100. For example, a user may be able to, via the interface presented on display 154, control the music output, door 106, window 160, camera 152, display 154, any other element of autonomous vehicle 100, or any combination thereof.

In some embodiments, autonomous vehicle 100 may include other sensors and controls. For example, circuitry 156 may control opening and closing of doors 106, opening and closing of windows 160, or opening and closing of any other door or windows of autonomous vehicle 100. In some embodiments, circuitry 156 may control seat belt mechanism 162. For example, circuitry 156 may prevent seat belt mechanism 162 from being disengaged during certain periods of time.

In some embodiments, autonomous vehicle 100 may include other features. In some embodiments, autonomous vehicle 100 may include speakers for playing sounds or music, or enabling a person to communicate with a person being transported, and a climate-control system for ventilating autonomous vehicle 100 and increasing or decreasing the temperature inside autonomous vehicle 100.

In some embodiments, autonomous vehicle 100 may include a plurality of other sensors 158. For example, autonomous vehicle 100 may include gas sensors (e.g., spectrum analyzers) configured to detect the presence of a specific gas and the concentration levels of that gas. In some embodiments, autonomous vehicle 100 may include one or more pressure sensors that may detect a presence of pressure at various points in the vehicle. In some embodiments, autonomous vehicle 100 may include one or more weight sensors that may detect weight at specific points in autonomous vehicle 100 or the total weight of autonomous vehicle 100.

In some embodiments, sensors 158 may include a hazard sensor or a plurality of hazard sensors for detecting concentration of a variety of gaseous, liquid or chemical hazardous materials. For example, hazard sensors may include one or more gas detectors. In some embodiments, gas detectors may include electrochemical sensors, pellistor sensors, photoionization sensors, infrared point sensors, infrared imaging sensors, any other gas sensor, or any combination thereof. In some embodiments, hazard sensors may include one or more liquid detectors or solid material detectors.

In some embodiments, hazard sensors may be configured to detect a concentration of specific chemicals elements or compounds. In some embodiments, such hazard sensors may provide the concentration data to circuitry 156. For example, hazard sensors may detect a concentration level of urea. In some embodiments, when a threshold level of urea is reached, circuitry 156 may detect a presence of urine in the vehicle. In another example, hazard sensors may detect concentration level of butyric acid. In some embodiments, when a threshold level of butyric acid is reached, circuitry 156 may detect a presence of vomit in the vehicle.

In some embodiments, hazard sensors may use a combination of sensors to detect a presence of a hazardous material (e.g., human-generated biohazardous material). For example, a presence of liquid having a certain ratio of chemical elements may be detected to be blood. In another example, a presence of a solid having a certain ratio of chemical elements may be detected to be stool (e.g., a mass spectrometry sensor can be used to analyze solids). In some embodiments, a presence of any other hazardous material may be detected by hazard sensors.

In some embodiments, non-chemical sensors may be used to detect a presence of a hazardous material. For example, data feed from camera 152 may be subject to image processing to detect presence of certain hazardous materials. For example, a presence of viscose red fluid on or next to human bodies may be interpreted as a presence of blood. In some embodiments, the video image may be further used to confirm the presence of blood, for example, by determining that the human body is the source of the blood. In another example, data feed from camera 152 may be used to detect presence of urine, stool, or vomit. In some embodiments, any other sensors of autonomous vehicle 100 may be used by themselves or in combination to detect the presence of a hazardous material.

In some embodiments, sensors 158 may include a liquid sensor (e.g., a sensor place in the floor of vehicle 100). For example, the liquid sensor may be in a place such that liquid collecting on the floor would eventually reach the liquid sensor. For example, the liquid sensor may be placed in a recess in the floor of the vehicle 100). Liquid may be channeled to the recess via slope or grooves in the floor of vehicle 100. In some embodiments, the liquid sensor may operate via color analysis, via chemical analysis, or via light spectrum analysis.

In some embodiments, sensors 158 may include a solid matter analyzer. For example, the solid matter analyzer may use mass spectrometry to calculate composition of solids.

In some embodiments, vehicle 100 may include additional feature 166. For example, feature 166 may include emergency oxygen masks which can be deployed from ceiling of vehicle 100. In some embodiments, oxygen or air may be provided to passengers over such masks. In some embodiments, feature 166 may include an aerosol dispenser.

For example, the aerosol dispenser may be configured to spray an aromatic compound into the interior of vehicle 100.

Figure 2:
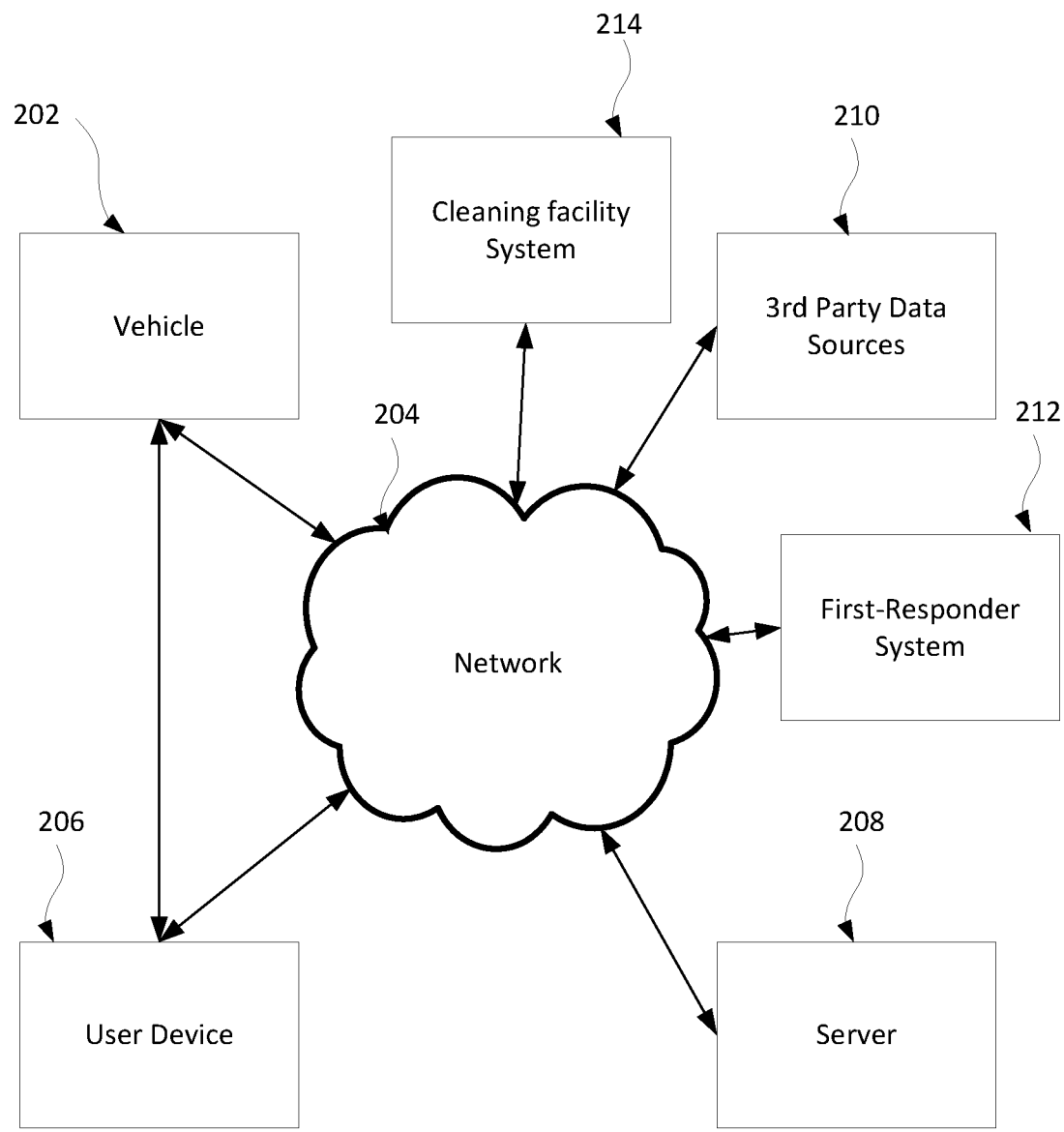
FIG. 2 shows a block diagram for a system for operating an autonomous vehicle, in accordance with some embodiments of the present disclosure.

FIG. 2 shows a block diagram for a system 200 for operating an autonomous vehicle in accordance with some embodiments of the present disclosure. System 200 may include vehicle 202 (e.g., autonomous vehicle 100), user device 206, server 208, and third-party data sources 210. In some embodiments, system 200 may also include a first-responder system 212. In some embodiments, system 200 may also include a cleaning facility system 214.

In some embodiments, system 200 may include network 204 communicatively interconnecting vehicle 202, user device 206, server 208, and third-party data sources 210. In some embodiments, network 204 may be the Internet, intranet, Bluetooth network, LAN, WAN, a Wi-Fi network, any other wired or wireless network, or any combination thereof.

In some embodiments, user device 206 may be a smartphone, a laptop, a computer, any consumer electronic device, or any combination thereof. In some embodiments, user device 206 may be communicatively connected to vehicle 202. In some embodiments, user device 206 may send commands and/or instructions to vehicle 202 via any kind of communicative connection (e.g., a direct connection or via network 204). For example, user device 206 may control functions of vehicle 202 via the communicative connection.

In some embodiments, user device 206 may be directly connected to vehicle 202. For example, user device 206 may be communicatively connected to vehicle 202 via Bluetooth or via NFC field. For example, circuitry 156 of FIG. 1 may include a Bluetooth or NFC transceiver for connecting to the device 202. In another example, user device 206 may be communicatively connected to vehicle 202 via a wired connection (e.g., via wired port located inside vehicle 202).

In some embodiments, user device 206 may be communicatively connected to vehicle 202 via network 204. For example, commands from user device 206 may be transmitted to vehicle 202 via network 204. For example, circuitry 156 of FIG. 1 may include a Wi-Fi or cellular transceiver for connecting to network 204. Similarly, vehicle 202 may send data and acknowledgements to user device 206 via network 204. In some embodiments, user device 206 may be connected to vehicle 202 via server 208. For example, user device 206 may send commands to server 208 (e.g., via network 204), while server 208 may forward these commands to vehicle 202.

In some embodiments, a user may control vehicle 202 via user device 206. For example, the user may enter the destination for vehicle 202. In some embodiments, the user may control elements of vehicle 202 via user device 206. For example, the user may open and close doors and windows, play music, play video, or control the climate-control system. In some embodiments, the user may control any other capability of vehicle 202 via input on user device 206 (e.g., via custom app or application executing on user device 206).

In some embodiments, server 208 may comprise a single web server. In some embodiments, server 208 may comprise a plurality of servers distributed in one or more facilities. In some embodiments, server 208 may provide information to vehicle 202 (e.g., information requested by user device 206). In some embodiments, vehicle 202 may be operated entirely via instructions executing on server 208. That is, server 208 may control all elements of vehicle 202 (e.g., elements of autonomous vehicle 100), while vehicle 202 may only have circuitry sufficient to send sensor data to server 208 and receive commands from server 208. In some embodiments, server 208 may connect to the network via a cellular transceiver for connecting to a cellular network (or via any other kind of transceiver).

In some embodiments, any of vehicle 202, user device 206, and server 208 may communicate to third-party data sources 210 via network 204. Third-party data sources 210 may include websites or private databases configured to provide requested data. For example, third-party data sources 210 may provide up-to-date traffic, weather, or financial information needed for operation of vehicle 202. In some embodiments, third-party data sources 210 may provide any other kind of data or information. For example, third-party data sources 210 may provide addressee or contact information for the closest (or most relevant) first-respond facility system (e.g., first-respond facility system 212) or closest (or most relevant) cleaning facility system (e.g., cleaning facility system 214).

In some embodiments, server 208 may comprise memory storing instructions for controlling vehicle 202. For example, a processor of server 208 may execute such instructions to generate a control signal. The control signal for controlling vehicle 202 may then be transmitted to vehicle 202 over network 204. Vehicle 202 may then be operated according to the received control signal.

In some embodiments, instructions for controlling vehicle may be distributed between vehicle 202, user device 206, server 208 or any combination thereof. In such embodiments, respective processors of vehicle 202, user device 206, server 208 may execute their part of the instructions or jointly generate a control signal for controlling vehicle 202.

For example, user device 206 may be used to transmit requests for a trip via an autonomous vehicle. In some embodiments, the request may be transmitted to server 208 via network 204. In some embodiments, server 208 may select a vehicle for a trip to the requested destination. For example, vehicle 202 may be selected based on location and availability of vehicle 202. In some embodiments, circuitry of vehicle 202 may then compute the route and configure itself based on the request. In some embodiments, vehicle 202 may then provide status information to server 208. Server 208 may then provide status information regarding vehicle 202 to user device 206 (or other user devices.)

In some embodiments, vehicle 202 may be communicatively connected to first-responder system 212 (e.g., via network 204). For example, first-responder system 212 may be a computer located at a first-responder facility and designed to provide information to first-response workers. In some embodiments, vehicle 202 may contact first-responder system 212 to provide necessary emergency response information. For example, if vehicle 202 has experienced an accident, vehicle 202 may automatically transmit vehicle location data, vehicle state data, and any other information to first-responder system 212 in order to enable more efficient first-responder actions. In some embodiments, if vehicle 202 has detected a hazardous material inside of vehicle 202, vehicle 202 may transmit this information to first-responder system 212 to enable the first responder to be prepared to deal with the type of expected hazard.

In some embodiments, vehicle 202 may be communicatively connected to cleaning facility system 214 (e.g., via network 204). For example, first-responder system 212 may be a computer located at a cleaning facility and designed to provide information to cleaning facility workers. In some embodiments, if vehicle 202 has detected a hazardous material inside of vehicle 202, vehicle 202 may transmit this information to cleaning facility system 214 to enable the cleaning facility to be prepared to clean the expected hazardous material.

Figure 3:
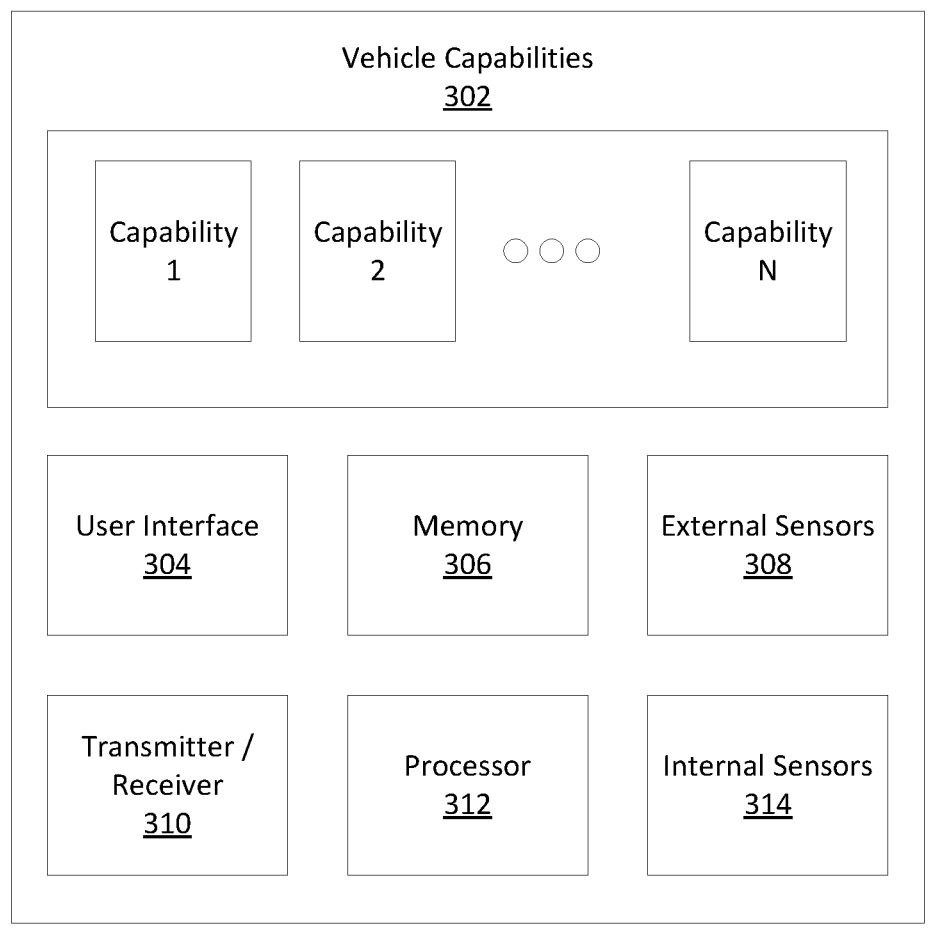
FIG. 3 shows a block diagram of components of an autonomous vehicle, in accordance with some embodiments of the present disclosure.

FIG. 3 shows a block diagram of components of autonomous vehicle 300 (e.g., autonomous vehicle 100 or vehicle 202), in accordance with some embodiments of the present disclosure. In some embodiments, vehicle 300 may include processor 312. Processor 312 may comprise a hardware CPU for executing commands stored in memory 306 or software modules, or combination thereof. In some embodiments, processor 312 may be a part of circuitry 156 of FIG. 1B.

In some embodiments, vehicle 300 may include memory 306. In some embodiments, memory 306 may be a part of circuitry 156 of FIG. 1B. In some embodiments, memory 306 may include hardware elements for non-transitory storage of commands or instructions, that, when executed by processor 312, cause processor 312 to operate vehicle 300 in accordance with embodiments described above and below.

In some embodiments, processor 312 may be communicatively connected to external sensors 308 (e.g., sensors 104 of FIG. 1A), internal sensors 314 (e.g., sensors 158 of FIG. 1B), transmitter/receiver 310, and user interface 304. External sensors 308 may include video sensors, audio sensors, gas sensors, pressure sensors, GPS sensors, LIDAR sensors, radar sensors, radio antennas, any other sensors, or any combination thereof. Internal sensors 314 may include video cameras, microphones, pressure sensors, weight sensors, gas sensors, sensors specific to vehicle capabilities 302, any other sensors, or any combination thereof.

In some embodiments, processor 312 may use data from external sensors 308 and internal sensors 314 to drive the vehicle and/or to perform other functions. In some embodiments, processor 312 may receive user input via user interface 304. In some embodiments, a user interface may include a screen (e.g., screen 154 of FIG. 1). In some embodiments, processor 312 may communicate with a user device (e.g., user device 206 of FIG. 2), a server (e.g., server 308 of FIG. 2), other data sources (e.g., third-party data sources 210 of FIG. 2), a first-responder system (e.g., first-responder system 212 of FIG. 2), and a cleaning facility system (e.g., cleaning facility system 212) via a network (e.g., network 204 of FIG. 2) that may be accessed via transmitter/receiver 310.

In some embodiments, vehicle 300 may include a plurality of capabilities 302 (e.g., capabilities 1-N). In some embodiments, each of capabilities 1-N may be controlled by processor 312. For example, processor 312 may gather inputs from any of the elements of vehicle 300, analyze the inputs, and enable or disable any of capabilities 1-N based on the analysis and based on the current mode of operation.

In some embodiments, capabilities 302 may include a window control capability. For example, vehicle 300 may include a user interface (e.g., a hardware or software switch) for opening and closing windows (e.g., windows 102 and 160 of FIGS. 1A-B). In some embodiments, windows may be controlled via input from a user device. In some embodiments, processor 312 may enable or disable the ability of the user to control windows at different times (e.g., based on the current mode of operation).

In some embodiments, capabilities 302 may include a door control capability. For example, vehicle 300 may include a user interface (e.g., a hardware or software switch) for opening and closing doors (e.g., door 106 of FIG. 1A). In some embodiments, doors may be controlled via input from a user device. In some embodiments, processor 312 may enable or disable the ability of the user to control doors at different times (e.g., based on the current mode of operation).

In some embodiments, capabilities 302 may include a route selection control capability. For example, vehicle 300 may include a user interface for route selection (e.g., via user interface 304). In some embodiments, the user may also be able to select a route via user device 206 of FIG. 2. In some embodiments, processor 312 may enable or disable the ability of the user to select a route at different times (e.g., based on the current mode of operation).

In some embodiments, capabilities 302 may include a music or radio selection control capability. For example, vehicle 300 may include a user interface for selecting music to be played. In some embodiments, music selection may be controlled via input from a user device (e.g., user device 206 of FIG. 2). In some embodiments, processor 312 may enable or disable the ability of the user to select music or radio stations at different times (e.g., based on the current mode of operation).

In some embodiments, capabilities 302 may include climate-control capability. For example, vehicle 300 may include a user interface for adjusting temperature inside vehicle 300 (e.g., via turning on or off fans, heaters, warmers, or air conditioning elements of vehicle 300). In some embodiments, the climate may be controlled via input from a user device (e.g., user device 206 of FIG. 2). In some embodiments, processor 312 may enable or disable the ability of the user to control the climate at different times (e.g., based on the current mode of operation).

In some embodiments, capabilities 302 may include e-commerce capability. For example, vehicle 300 may include a user interface for making purchases. In some embodiments, purchases may be made via a user voice command, or via interface displayed on display 154. In some embodiments, processor 312 may enable or disable the ability of the user to engage in e-commerce at different times (e.g., based on the current mode of operation).

In some embodiments, capabilities 302 may include a seat belt unlocking capability. For example, vehicle 300 may include a user interface (e.g., a hardware button or software switch) for disengaging a seat belt (e.g., via seat belt mechanism 162 of FIG. 1B). In some embodiments, a seat belt may be engaged or disengaged via input from a user device (e.g., user device 206 of FIG. 2). In some embodiments, processor 312 may enable or disable seat belt unlocking capability at different times (e.g., based on the current mode of operation).

In some embodiments, capabilities 302 may include Internet access capability. For example, vehicle 300 may include a user interface for accessing websites via the Internet. In some embodiments, the Internet access may be provided via display 154 of FIG. 1B. In some embodiments, vehicle 300 may provide a Wi-Fi signal enabling user device 206 of FIG. 2 to access the Internet. In some embodiments, processor 312 may enable or disable the ability of the user to access the Internet at different times (e.g., based on the current mode of operation).

In some embodiments, capabilities 302 may include an autonomous vehicle location reporting capability. In some embodiments, processor 312 may be able to determine the current location of vehicle 300 (e.g., via GPS input). In some embodiments, processor 312 may be able to report the current location of vehicle 300 to an external device (e.g., user device 206 of FIG. 2, server 208 of FIG. 2, first-responder system 212 of FIG. 2, or any other device). In some embodiments, processor 312 may enable or disable location reporting capability at different times (e.g., based on the current mode of operation).

In some embodiments, capabilities 302 may include password control capability. In some embodiments, other capabilities 302 may be enabled or disabled only when a password is entered (e.g., via user interface 304). For example, if the user desires to input a new destination, processor 312 may require the user to meet a password challenge if the password control capability is enabled. In some embodiments, processor 312 may enable or disable the password control capability at different times (e.g., based on the current mode of operation).

In some embodiments, capabilities 302 may include a camera feed capability. In some embodiments, processor 312 may be able to gather video feed data from cameras inside or outside of the vehicle (e.g., camera 152 of FIG. 1B). In some embodiments, processor 312 may be able to send the camera feed to an external device (e.g., user device 206 of FIG. 2, server 208 of FIG. 2, first-responder system 212 of FIG. 2, and cleaning facility system 212 of FIG. 2, or any other device). In some embodiments, processor 312 may enable or disable camera feed capability at different times (e.g., based on the current mode of operation).

In some embodiments, capabilities 302 may include a sound feed capability. In some embodiments, processor 312 may be able to gather sound feed data from microphones inside or outside of the vehicle (e.g., a camera 152 of FIG. 1B may include a microphone). In some embodiments, processor 312 may be able to send the sound feed to an external device (e.g., user device 206 of FIG. 2, server 208 of FIG. 2, first-responder system 212 of FIG. 2, or any other device). In some embodiments, processor 312 may enable or disable sound feed capability at different times (e.g., based on the current mode of operation).

In some embodiments, capabilities 302 may include a capability to detect a presence of hazardous materials. For example, processor 312 may receive an input from one or more sensors (e.g., sensors disposed in FIGS. 1A and 1B) and determine the presence of particular hazardous gasses, liquids or solids. For example, processor 312 may determine the presence of urine, vomit, stool, blood, any other human-generated biohazardous material, or any combination of the above.

In some embodiments, capabilities 302 may include capabilities designed to counteract or address the presence of hazardous materials. For example, processor 312 may activate increased air circulation, open or close the windows, engage additional filtering, distribute life support devices (e.g., breathing masks), use any other feature of vehicle 300 designed to counteract or address the presence of hazardous materials, or perform any combination of the aforementioned steps.

In some embodiments, capabilities 302 may include capabilities designed to counteract or address the presence of hazardous materials by adjusting or modifying the current route of vehicle 300. For example, processor 312 may add an emergency stop to the route, to allow the users to immediately exit vehicle 300. In some embodiments, processor 312 may redirect vehicle 300 to a first-responder facility (e.g., an emergency room) or to a cleaning facility (e.g., a car wash). In some embodiments, such redirection may be performed after the additional stop is made. In some embodiments, such redirection may be performed without an additional stop (e.g., when a passenger needs to be delivered to the first-responder facility).

Figure 4:
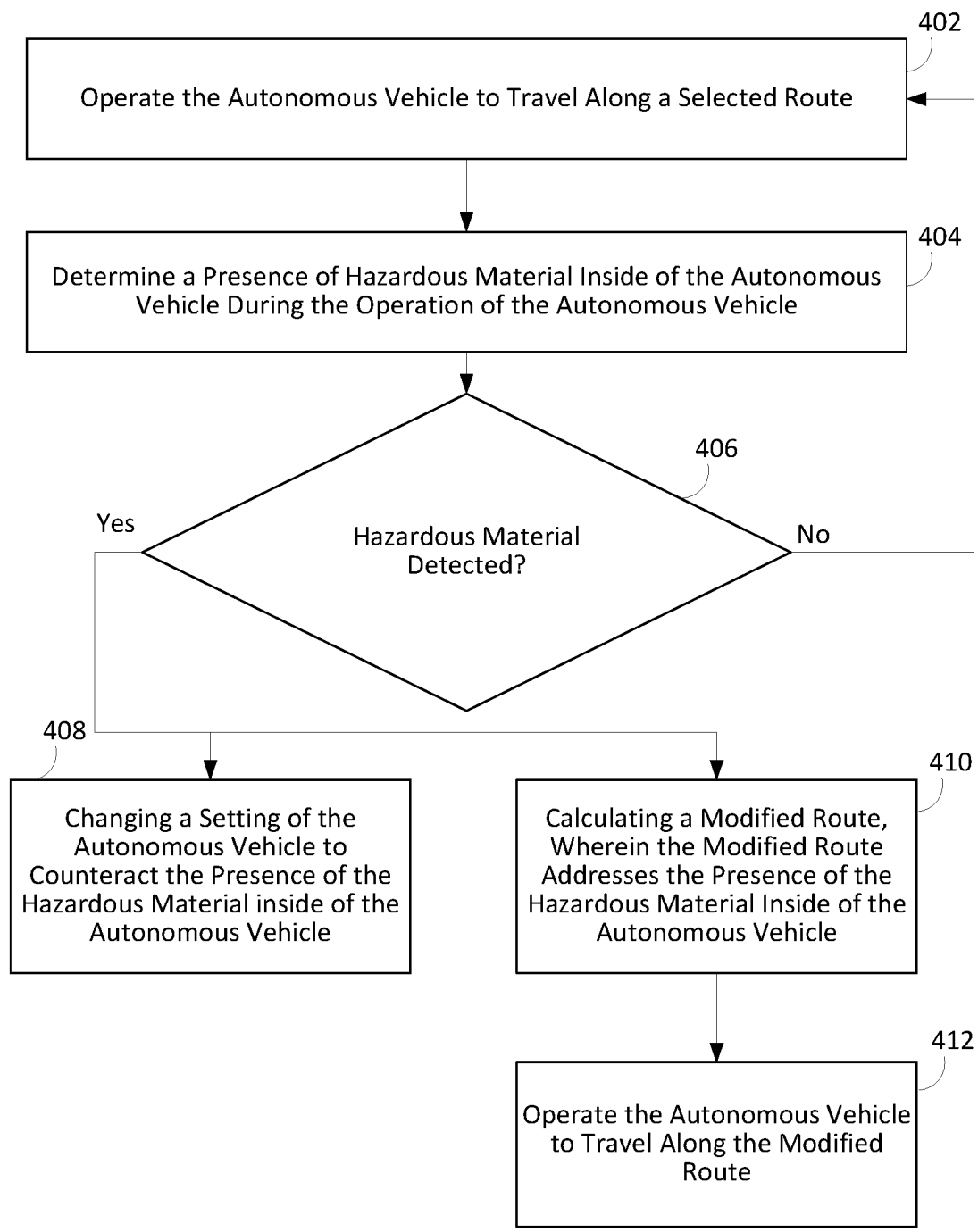
FIG. 4 depicts an illustrative flow diagram for a process of operating an autonomous vehicle when hazardous material is detected, in accordance with some embodiments of the disclosure.

FIG. 4 depicts an illustrative flow diagram of a process 400 of operating an autonomous vehicle when hazardous material is detected, in accordance with several embodiments of the disclosure. In some embodiments, process 400 may be executed by the processing circuitry of an autonomous vehicle 100 (FIGS. 1A-B), 202 (FIG. 2), or 300 (FIG. 3). In some embodiments, the processing circuitry may be one of circuitry 156 of FIG. 1B or processor 312 of FIG. 3. In some embodiments, the processing circuitry may perform process 400 by execution of instructions stored in memory (e.g., memory 306 of FIG. 3). In some embodiments, the processing circuitry may be a part of server 208 of FIG. 2, which may control autonomous vehicle 202 via a command transmitted over network 204. In some embodiments, the processing circuitry may be distributed across multiple devices.

Process 400 begins at 402, where the processing circuitry operates the autonomous vehicle to travel along a selected route. For example, the autonomous vehicle may be a taxi that was requested by a user (e.g., via user device 206 of FIG. 2) to travel from an origin geographical point to a destination geographical point. In some embodiments, the processing circuitry may determine the origin point using a GPS sensor, while the address of the destination point may be received as an input from a user via either a user device or an interface of the autonomous vehicle. In some embodiments, after the selected route between the origin and the destination is calculated, the autonomous vehicle may travel along the selected route without further human input.

Process 400 continues at 404, where the processing circuitry may determine, using a sensor or sensors (e.g., one or more of the sensors 158 of FIG. 1B), whether hazardous material is present inside the autonomous vehicle during the operation of the autonomous vehicle. For example, the processing circuitry may receive an input from a gas sensor indicating a concentration level of certain chemical compound. In some embodiments, the processing circuitry may determine whether a presence of a biohazard when the concentration level of a chemical compound exceeds a threshold level set for that chemical compound.

For example, if the processing circuitry detects that the level of urea exceeds a threshold level, the processing circuitry may determine that urine is present inside the autonomous vehicle. In another example, if the processing circuitry detects that the level of butyric acid exceeds a threshold level, the processing circuitry may determine that vomit is present inside the autonomous vehicle.

In some embodiments, the processing circuitry may use data from any other sensor or combination of the sensors to determine a presence of any other hazardous material, biohazardous material, or human-generated biohazardous material. For example, the processing circuitry may determine the presence of $CO_2$, human stool, bile, radioactive material, bacterial material, or any other hazardous material.

In some embodiments, the processing circuitry may use data from a camera to detect presence of a hazardous material. For example, if a video feed includes red liquid, the processing circuitry may detect a presence of blood.

In some embodiments, the processing circuitry may use data from a microphone to detect a presence of a hazardous material. For example, if a user is saying "There is vomit everywhere," the processing circuitry may determine the presence of vomit.

In some embodiments, the processing circuitry may use the audio and video feed in combination with other sensors. For example, if a user is saying "There is vomit everywhere," the processing circuitry may activate a butyric acid sensor, and lower the butyric acid concentration threshold for detecting human vomit.

At 406, in response to determining that hazardous material is not present, the processing circuitry may proceed to step 402 and continue operating the vehicle along the original route. In some embodiments, at 406, in response to determining the presence of a hazardous material, the processing circuitry may enter into a hazard mode. In some embodiments, while in a hazard mode, the processing circuitry may take one or more actions designed to mitigate or address the presence of a hazardous material. In some embodiments, the processing circuitry may proceed to simultaneously or sequentially perform steps 408 and 410-412. In some embodiments, steps 408 and 410-412 may be performed individually or sequentially. In some embodiments, other steps to mitigate or address the presence of a hazardous material may be taken by the processing circuitry in addition to, instead of, or sequentially with steps 408 and 410-412.

In some embodiments, at 408, the processing circuitry may change a setting of the autonomous vehicle to counteract the presence of the hazardous material inside the autonomous vehicle. For example, the processing circuitry may open one or more windows of the autonomous vehicle.

In some embodiments, the processing circuitry may increase the ventilation of air in the autonomous vehicle. For example, the processing circuitry may set the fan setting of an air conditioning system to maximum. In some embodiments, the processing circuitry may activate additional filters designed for a particular biohazard. In some embodiments, the processing circuitry may deploy life support devices. For example, if the air inside the vehicle is determined to be of very poor quality, the processing circuitry may deploy emergency system oxygen masks to enable the passenger to breathe.

In some embodiments, at 408, the processing circuitry may calculate a modified route, wherein the modified route addresses the presence of the hazardous material inside the autonomous vehicle. The modified route may be calculated differently depending on the type of a present hazard.

For example, if the hazard is merely inconvenient, the processing circuitry may query the user if they wish to exit vehicle. If the user responds affirmatively (e.g., via user interface 304 of FIG. 3 or via user device 206 of FIG. 2), the processing circuitry may add a stop to the selected route that would enable the user to safely exit the vehicle. For example, the processing circuitry may use map data and current positions of the autonomous vehicle to find a safe disembarking location. For example, the processing circuitry may identify a nearest rest stop, gas station, or public transportation terminal. In some embodiments, the processing circuitry may replace the current destination with an alternative stop. Subsequently, the processing circuitry may modify the route to drive to the identified location for disembarking.

In some embodiments, if the hazard is dangerous, the processing circuitry may add an immediate stop to the route. For example, the processing circuitry may determine that the vehicle should pull over as soon as possible. In that case, the processing circuitry may add a stopping location on the shoulder of the road close to the current location of the vehicle. In some embodiments, the processing circuitry may add a location of a first-responder facility or a cleaning facility to the route. In some embodiments, the vehicle may terminate any further navigation after making the immediate stop.

In some embodiments, at 412, the processing circuitry may operate the autonomous vehicle to travel along the modified route. For example, the processing circuitry may drive the autonomous vehicle to the new stop or to the new destination added to the modified route. In some embodiments, the processing circuitry may also warn the user regarding the change in destination. For example, a warning may be displayed in display 154 of FIG. 1 or on user device 206 of FIG. 2. In some embodiments, the user may be able to override the change in the route, e.g., by issuing an override command via interface 304 of FIG. 3, or via user device 206 of FIG. 2.

Figure 5:
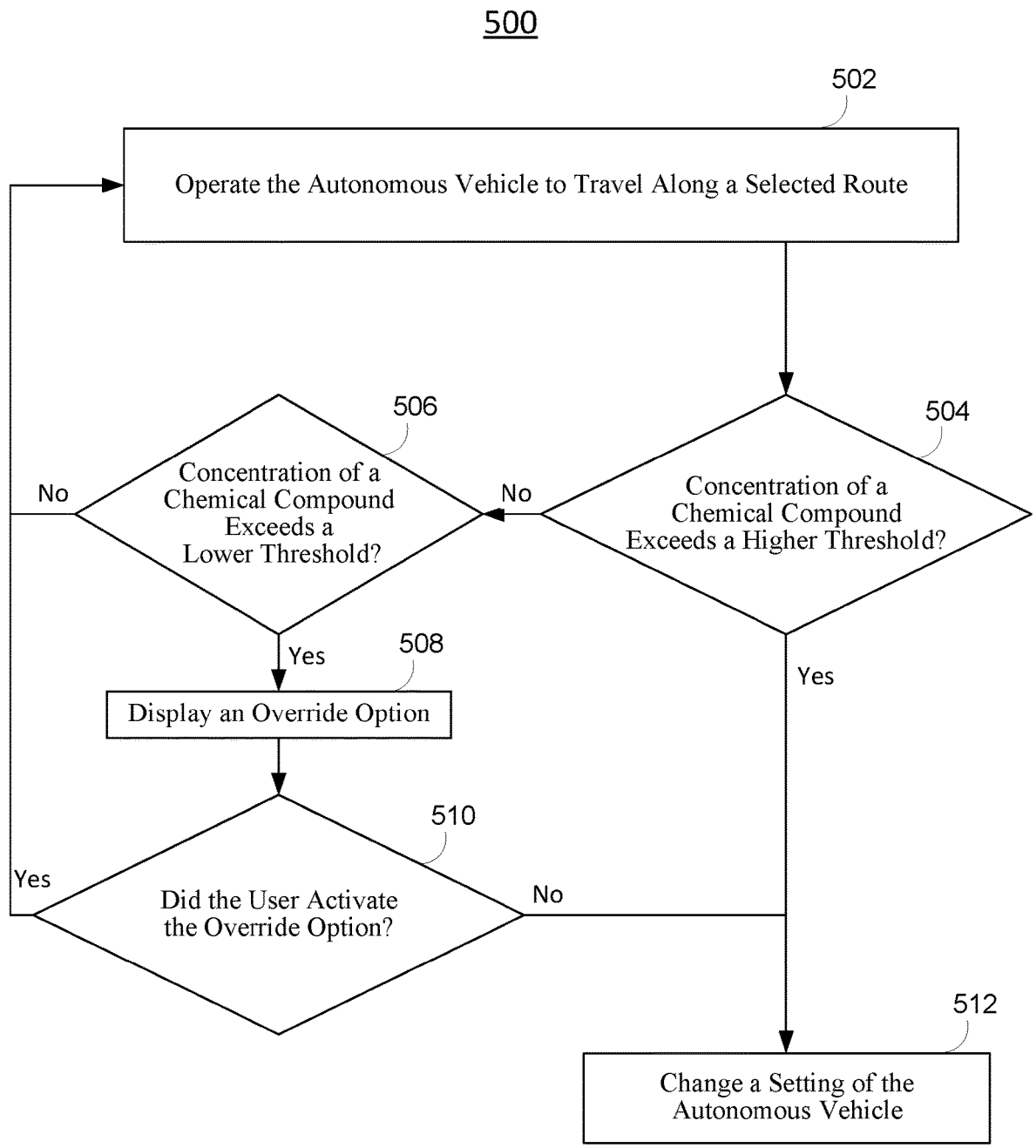
FIG. 5 depicts an illustrative flow diagram for a process of changing a setting of an autonomous vehicle, in accordance with some embodiments of the disclosure.

FIG. 5 depicts an illustrative flow diagram of a process 500 for changing a setting of an autonomous vehicle, in accordance with an embodiment of the disclosure. In some embodiments, process 500 may be executed by a processing circuitry of autonomous vehicle 100 (FIGS. 1A-B), 202 (FIG. 2), or 300 (FIG. 3). In some embodiments, the processing circuitry may be one of circuitry 156 of FIG. 1B or processor 312 of FIG. 3. In some embodiments, the processing circuitry may perform process 500 by execution of instructions stored in memory (e.g., memory 306 of FIG. 3). In some embodiments, processing circuitry may be a part of server 208 of FIG. 2, which may control autonomous vehicle 202 via a command transmitted over network 204. In some embodiments, process 500 is performed as part of one or more steps displayed as part of FIG. 4.

Process 500 begins at 502, where the processing circuitry may operate the autonomous vehicle to travel along a selected route. In some embodiments, this step is performed as described with respect to step 402 of FIG. 4.

In some embodiments, at 504, the processing circuitry may determine whether a concentration of a particular chemical compound exceeds a higher threshold that is greater than a lower threshold. In some embodiments, if the concentration of a particular chemical compound does not exceed the higher threshold, process 500 may continue at step 506. In some embodiments, if the concentration of a particular chemical compound exceeds the higher threshold, process 500 may go directly to step 512. For example, when the concentration of urea gets to be very high, the processing circuitry may determine that the ride is too dangerous to continue regardless of the wishes of the user.

In some embodiments, at 512, the processing circuitry may change a setting of the autonomous vehicle as described in step 408 of FIG. 4. In some embodiments, at 518, the processing circuitry may also or alternatively modify the route of the autonomous vehicle as described in steps 410-412 of FIG. 4.

At 506, the processing circuitry may determine whether a concentration of a certain chemical compound (e.g., urea) exceeds the lower threshold (e.g., whether the concentration of a certain chemical is above a lower threshold but below the higher threshold). In some embodiments, a moderate concentration of urea may indicate a presence of contained or uncontained human urine in the autonomous vehicle. In some embodiments, if the concentration of the certain chemical compound does not exceed the lower threshold, the processing circuitry may proceed back to step 502 and continue operating the autonomous vehicle along the selected route using the existing settings. In some embodiments, if the concentration of the certain chemical compound exceeds the lower threshold (but does not exceed the higher threshold), the processing circuitry may proceed to step 508.

At 508, the processing circuitry may present an override option to the user. For example, if a certain amount of urea is detected, the processing circuitry may be unsure whether an action needs to be taken. For example, an increase in urea concentration may occur when a baby passenger urinates in a diaper, or if the urine is otherwise contained. In such circumstances, a passenger may be given a chance to override actions that would otherwise automatically be performed in a presence of hazardous materials. In some embodiments, the override option may be presented via interface 304 of FIG. 3, or user device 206 of FIG. 2.

In some embodiments, at 510, the processing circuitry may determine whether the user has activated the override option. If the override option was activated (e.g., a use user has pressed an "override" button or issued an "override" voice command), the processing circuitry may proceed back to step 502. If the override option was not activated, the processing circuitry may proceed to step 512. In some embodiments, the processing circuitry may proceed to step 512 after a certain delay (e.g., after 20 seconds). In some embodiments, while the override option is displayed, the processing circuitry may continue monitoring the concentration level of the chemical compound. In some embodiments, if the processing circuitry determines that the concentration level of the chemical compound has changed to exceed the higher threshold, the processing circuitry may remove the display of the override option, and proceed to step 512.

Figure 6:
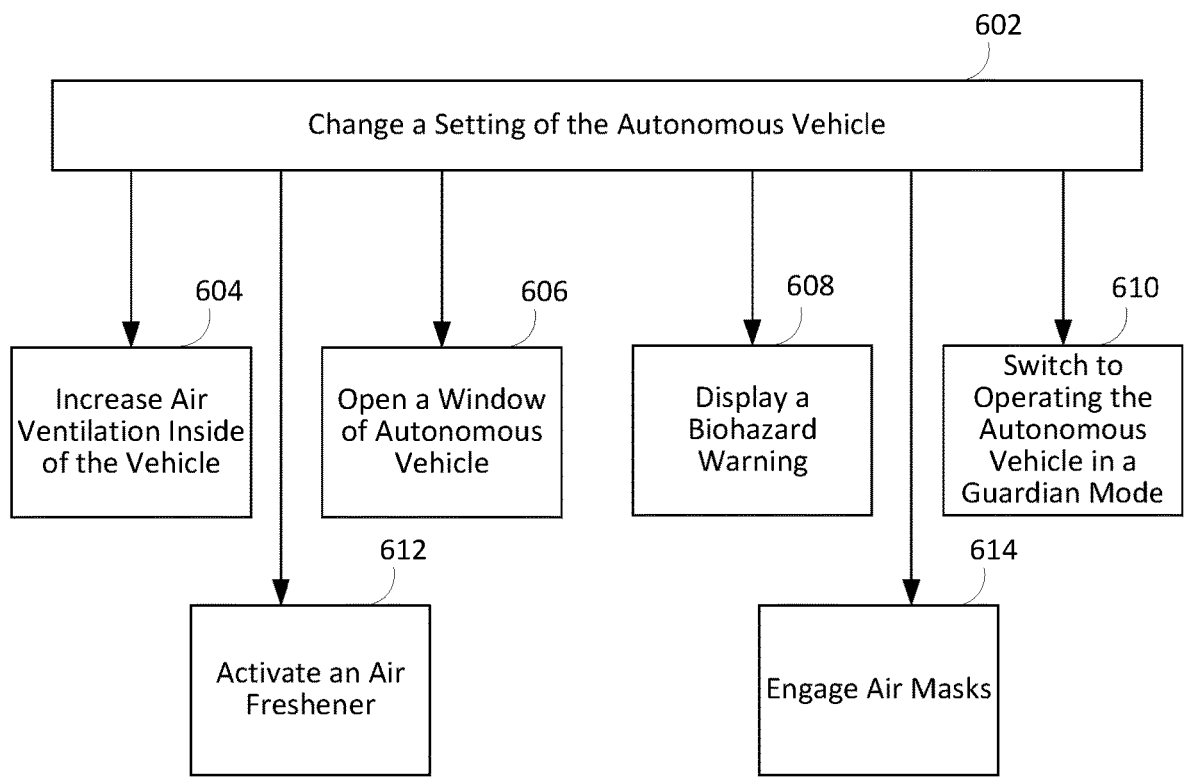
FIG. 6 depicts another illustrative flow diagram for a process of changing a setting of an autonomous vehicle, in accordance with some embodiments of the disclosure.

FIG. 6 depicts an illustrative flow diagram of a process 600 for changing a setting of an autonomous vehicle, in accordance with an embodiment of the disclosure. In some embodiments, process 600 may be executed by the processing circuitry of an autonomous vehicle 100 (FIGS. 1A-B), 202 (FIG. 2), or 300 (FIG. 3). In some embodiments, the processing circuitry may be one of circuitry 156 of FIG. 1 or processor 312 of FIG. 3. In some embodiments, the processing circuitry may perform process 500 by execution of instructions stored in memory (e.g., memory 306 of FIG. 3). In some embodiments, processing circuitry may be a part of server 208 of FIG. 2, which may control autonomous vehicle 202 via a command transmitted over network 204. In some embodiments, process 600 is performed as part of step 408 of FIG. 4.

Process 600 begins at 602, where the processing circuitry may change a setting of the autonomous vehicle. For example, the processing circuitry may perform step 602 in response to determining a presence of hazardous material, e.g., as described in steps 404-406 of FIG. 4. In some embodiments, changing the setting may be done by performing any one of, several of, or all of steps 602-614. In some embodiments, steps 602-614 may be performed individually, optionally, sequentially, or simultaneously by the processing circuitry.

In some embodiments, at 604 the processing circuitry may increase air ventilation inside the autonomous vehicle. For example, the processing circuitry may set the fan setting of the air conditioning system to maximum. In some embodiments, the processing circuitry may activate emergency fans of the autonomous vehicle.

In some embodiments, at 606 the processing circuitry may fully or partially open one or more windows of the autonomous vehicle. In some embodiments, the processing circuitry may open the windows in a way calculated to provide maximum airflow to the location of the hazardous material. For example, if the hazardous material is located on the back-left seat of the autonomous vehicle, the processing circuitry may open the front right window and back left window to maximize the airflow flow away from the back-left seat.

In some embodiments, at 608, the processing circuitry may display a biohazard warning. For example, the warning may be displayed on the outside of the autonomous vehicle (e.g., using display 108 of FIG. 1). For example, the outside display may display the text "Warning Biohazard Inside!"

In some embodiments, at 610, the processing circuitry may switch operation of a vehicle to a guardian mode. In some embodiments, the processing circuitry may determine that the user is no longer competent to use all options of the autonomous vehicle. For example, the user may be passed out or otherwise impaired. In some embodiments, the processing circuitry may then engage the guardian mode. In some embodiments, while the autonomous vehicle is operating in the guardian some capabilities of the autonomous vehicle may be disabled for the user. For example, the user may become-unable to change the destination, or alter the ventilation settings. Guardian mode operations are described more fully in a co-pending application title "Systems and Methods for Operating an Autonomous Vehicle in a Guardian Mode," U.S. application Ser. No. 16/006,536, now patented as U.S. Pat. No. 10,780,888, which is incorporated herein in its entirety.

In some embodiments, at 612 the processing circuitry may activate an air freshener. For example, the processing circuitry may spray an aerosol designed to cover up a noxious smell produced by a hazardous material.

In some embodiments, at 614 the processing circuitry may engage air masks. For example, air mask may be dropped from the ceiling of a vehicle such that the user may easily pull an air mask over his or her face.

Figure 7:
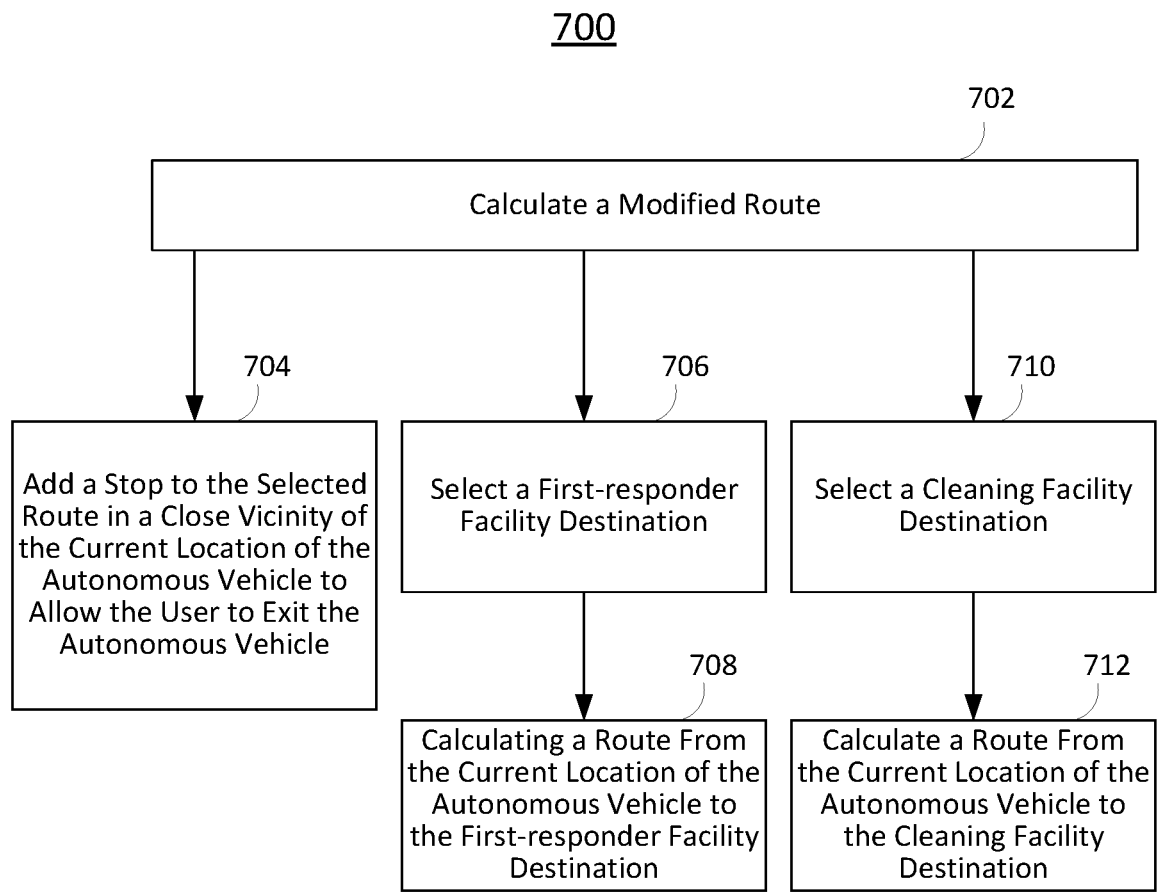
FIG. 7 depicts an illustrative flow diagram for a process of calculating a modified route for an autonomous vehicle, in accordance with some embodiments of the disclosure.

FIG. 7 depicts an illustrative flow diagram of process 700 for calculating a modified route for an autonomous vehicle, in accordance with some embodiments of the disclosure. In some embodiments, process 700 may be executed by a processing circuitry of an autonomous vehicle 100 (FIGS. 1A-B), 202 (FIG. 2), or 300 (FIG. 3). In some embodiments, the processing circuitry may be one of circuitry 156 of FIG. 1B or processor 312 of FIG. 3. In some embodiments, the processing circuitry may perform process 500 by execution of instructions stored in memory (e.g., memory 306 of FIG. 3). In some embodiments, processing circuitry may be a part of server 208 of FIG. 2, which may control autonomous vehicle 202 via a command transmitted over network 204. In some embodiments, process 700 is performed as part of step 412 of FIG. 4.

Process 700 begins at 702, where the processing circuitry may calculate a modified route for an autonomous vehicle. For example, the processing circuitry may perform step 702 in response to determining a presence of hazardous material, e.g., as described in steps 404-406 of FIG. 4. In some embodiments, changing the calculation of a modified route may be done by performing any one of, several of, or all of steps 704, 706-708, and 710-712. In some embodiments, steps 704, 706-708, and 710-712 may be performed individually, optionally, sequentially, or simultaneously by the processing circuitry.

In some embodiments, at 704, the processing circuitry may add a stop to the selected route in a close vicinity of the current location of the autonomous vehicle to allow the user to exit the autonomous vehicle. For example, the processing circuitry may identify a road shoulder spot close to the current location of the autonomous vehicle and add that location as a stop to the selected route. In some embodiments, the processing circuitry may also prompt the user to exit the vehicle once the additional or alternative stop is reached. In some embodiments, the vehicle may terminate any further navigation after making the immediate stop.

In some embodiments, at 706, the processing circuitry may determine that a first-responder facility is needed. For example, the processing circuitry may have determined that the health of a passenger is at risk (e.g., the passenger is losing a lot of blood.) In some embodiments, the processing circuitry may use map data to select an appropriate first-responder facility. In some embodiments, the map data may be provided by third party services (e.g., by third-party sources 210 of FIG. 2).

For example, the processing circuitry may determine a location of the emergency room closest to the current location of the autonomous vehicle.

At 708, the processing circuitry may calculate a route from the current location of the autonomous vehicle to the first-responder facility destination. In some embodiments, the processing circuitry may then include the calculated route as a part of the modified route. In some embodiments, the processing circuitry may notify the user about the new destination of the autonomous vehicle. In some embodiments, the processing circuitry may send a notification to the selected first-responder facility (e.g., via network 204). In some embodiments, the notification may include the type of hazardous material that was detected to enable the first-response workers to handle the hazardous material, and the consequences of the hazardous material.

In some embodiments, at 710, the processing circuitry may determine that a cleaning facility is needed. For example, the processing circuitry may have determined that the hazardous material needs to be cleaned. In some embodiments, the processing circuitry may use map data to select an appropriate cleaning facility. For example, the processing circuitry may determine a location of the car wash closest to the current location of the autonomous vehicle.

In some embodiments, at 710, the processing circuitry may determine that a cleaning facility is needed. For example, the processing circuitry may have determined that the vehicle contains hazardous material that needs to be cleaned. In some embodiments, the processing circuitry may use map data to select an appropriate cleaning facility. For example, the processing circuitry may determine a location of car wash closest to the current location of the autonomous vehicle.

At 712, the processing circuitry may calculate a route from the current location of the autonomous vehicle to the cleaning facility destination. In some embodiments, the processing circuitry may then include the calculated route as a part of the modified route. In some embodiments, the processing circuitry may notify the user about the new destination of the autonomous vehicle. In some embodiments, the processing circuitry may send a notification to the selected cleaning facility (e.g., via network 204). In some embodiments, the notification may include the type of hazardous material that was detected to enable the cleaning facility workers to clean that particular type of hazardous material.

It is contemplated that the steps or descriptions of each of FIGS. 4-7 may be used with any other embodiment of this disclosure. It is contemplated that some steps or descriptions of each of FIGS. 4-7 may be optional and may be omitted in some embodiments. In addition, the steps and descriptions described in relation to FIGS. 4-7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-3 could be used to perform one or more of the steps in FIGS. 4-7.

It will be apparent to those of ordinary skill in the art that methods involved in the present disclosure may be embodied in a computer program product that includes a computer-usable and/or readable medium. For example, such a computer-usable medium may consist of a read-only memory device, such as a CD-ROM disk or conventional ROM device, or a random-access memory, such as a hard drive device or a computer diskette, having a computer-readable program code stored thereon. It should also be understood that methods, techniques, and processes involved in the present disclosure may be executed using processing circuitry. The processing circuitry, for instance, may be a general-purpose processor, a customized integrated circuit (e.g., an ASIC), or a field-programmable gate array (FPGA) within vehicle 300 of FIG. 3.

The processes discussed above in FIGS. 4-7 are intended to be illustrative and not limiting. One skilled in the art would appreciate that the steps of the processes in FIGS. 4-7 discussed herein may be omitted, modified, combined, and/or rearranged, and any additional steps may be performed without departing from the scope of the disclosure. More generally, the above disclosure is meant to be exemplary and not limiting. Only the claims that follow are meant to set bounds as to what the present invention includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The foregoing is merely illustrative of the principles of this disclosure, and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for operating an autonomous vehicle, the method comprising:
   operating the autonomous vehicle to travel along a selected route;
   determining, using a sensor, an amount of hazardous material inside the autonomous vehicle during the operation of the autonomous vehicle; and
   in response to determining that the amount of hazardous material exceeds a first threshold:
      changing a setting of the autonomous vehicle to counteract a presence of the hazardous material inside the autonomous vehicle;
      calculating a modified route, wherein the modified route addresses the presence of the hazardous material inside the autonomous vehicle;
      operating the autonomous vehicle to travel along the modified route; and
      displaying an override option, wherein activation of the override option cancels the setting change and causes the autonomous vehicle to travel along the selected route; and
   in response to determining that the amount of the hazardous material in the autonomous vehicle subsequently exceeds a second threshold, removing the display of the override option.

2. The method of claim 1, wherein the hazardous material is a human-generated biohazardous material, wherein a human-generated biohazardous material comprises at least one of human vomit, human blood, human stool, and human urine.

3. The method of claim 1, wherein the sensor comprises a gas analyzer, and wherein the amount of the hazardous material comprises a concentration of a chemical compound.

4. The method of claim 3, wherein the chemical compound comprises at least one of butyric acid and urea.

5. The method of claim 1, wherein changing a setting of the autonomous vehicle comprises increasing air ventilation inside the vehicle.

6. The method of claim 1, wherein changing a setting of the autonomous vehicle comprises opening a window of the autonomous vehicle.

7. The method of claim 1, wherein calculating the modified route comprises adding a stop to the selected route in a vicinity of the current location of the autonomous vehicle to allow the user to exit the autonomous vehicle.

8. The method of claim 1, wherein calculating the modified route comprises:
selecting a first-responder facility destination; and
calculating a route from the current location of the autonomous vehicle to the first-responder facility destination.

9. The method of claim 8, wherein calculating the modified route comprises:
providing information indicative of the presence of hazardous material inside the autonomous vehicle to the first-responder facility.

10. The method of claim 1, wherein calculating the modified route comprises:
selecting a cleaning facility destination; and
calculating a route from the current location of the autonomous vehicle to the cleaning facility destination.

11. The method of claim 10, wherein calculating the modified route comprises:
providing information indicative of the presence of hazardous material inside the autonomous vehicle to the cleaning facility.

12. The method of claim 1, wherein determining the amount of hazardous material inside the autonomous vehicle comprises:
receiving video input from a camera located inside the autonomous vehicle; and
determining that the video input includes an indication of hazardous material.

13. The method of claim 1, further comprising:
displaying a biohazard warning on an outside surface of the autonomous vehicle while the autonomous vehicle travels along the modified route.

14. A system for operating an autonomous vehicle, the system comprising:
circuitry configured to:
operate the autonomous vehicle to travel along a selected route;
determine, using a sensor, an amount of hazardous material inside the autonomous vehicle during the operation of the autonomous vehicle; and
in response to determining that the amount of hazardous material exceeds a first threshold:
change a setting of the autonomous vehicle to counteract a presence of the hazardous material inside the autonomous vehicle;
calculate a modified route, wherein the modified route addresses the presence of the hazardous material inside the autonomous vehicle;
operate the autonomous vehicle to travel along the modified route;
display an override option, wherein activation of the override option cancels the setting change and causes the autonomous vehicle to travel along the selected route; and
in response to determining that the amount of the hazardous material in the autonomous vehicle subsequently exceeds a second threshold, remove the display of the override option.

15. The system of claim 14, wherein the hazardous material is a human-generated biohazardous material, wherein a human-generated biohazardous material comprises at least one of human vomit, human blood, human stool, and human urine.

16. The system of claim 14, wherein the sensor comprises a gas analyzer, and wherein the amount of the hazardous material comprises a concentration of a chemical compound.

17. The system of claim 16, wherein the chemical compound comprises at least one of butyric acid and urea.

18. The system of claim 14, wherein, while calculating the modified route, the circuitry is configured to:
add a stop to the selected route in a vicinity of the current location of the autonomous vehicle to allow the user to exit the autonomous vehicle.

* * * * *